US007972364B2

(12) United States Patent
Biedermann et al.

(10) Patent No.: US 7,972,364 B2
(45) Date of Patent: Jul. 5, 2011

(54) LOCKING ASSEMBLY FOR SECURING A ROD MEMBER IN A RECEIVER PART FOR USE IN SPINAL OR TRAUMA SURGERY, BONE ANCHORING DEVICE WITH SUCH A LOCKING ASSEMBLY AND TOOL THEREFOR

(75) Inventors: Lutz Biedermann, VS-Villingen (DE); Wilfried Matthis, Weisweil (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 1098 days.

(21) Appl. No.: 11/729,444

(22) Filed: Mar. 28, 2007

(65) Prior Publication Data

US 2009/0012567 A1 Jan. 8, 2009

Related U.S. Application Data

(60) Provisional application No. 60/787,901, filed on Mar. 31, 2006.

(30) Foreign Application Priority Data

Mar. 31, 2006 (EP) .................................... 06006832

(51) Int. Cl.
*A61B 17/70* (2006.01)
*A61B 17/86* (2006.01)

(52) U.S. Cl. ......................... 606/267; 606/270; 606/306

(58) Field of Classification Search .......... 606/264–270, 606/272, 300, 301, 305–308
See application file for complete search history.

(56) References Cited

U.S. PATENT DOCUMENTS 6,063,090 A * 5/2000 Schlapfer ..................... 606/270
(Continued)

FOREIGN PATENT DOCUMENTS

| | | | |
|---|---|---|---|
| CA | 2133484 | | 1/1995 |
| EP | 0465158 | A2 | 1/1992 |
| EP | 1604617 | A1 | 12/2005 |
| FR | 2869523 | A1 | 11/2005 |
| WO | WO 95/01132 | A1 | 1/1995 |

OTHER PUBLICATIONS

European Search Report for European Application No. 06006832.7-2318 dated Aug. 17, 2006 and mailed Aug. 29, 2006, 10pp.

*Primary Examiner* — Eduardo C Robert
*Assistant Examiner* — Ellen C Hammond
(74) *Attorney, Agent, or Firm* — Christie, Parker & Hale, LLP

(57) ABSTRACT

A locking assembly for securing a rod in a receiving part of a bone anchoring device includes a first locking element having a first end and a second end and a longitudinal axis of rotation and an outer surface provided with an external thread, a coaxial bore passing entirely through said first locking element and an internal thread provided at said bore, a second locking element having a: longitudinal axis of rotation and an outer surface with an external thread cooperating with the internal thread of said first locking element. The first locking element has a recess between the first end and the second end, that defines a circumferentially closed wall portion. The interior of the wall portion has a longitudinally extending structure for engagement with a tool. Furthermore, a tool is provided which has sections which can be independently engaged with the first and second locking element, respectively.

32 Claims, 8 Drawing Sheets

32 38 1 31 37 20 18 19 15 12 13 11 5 4 2

U.S. PATENT DOCUMENTS

| | | | | |
|---|---|---|---|---|
| 6,077,262 | A * | 6/2000 | Schlapfer et al. | 606/305 |
| 6,224,598 | B1 | 5/2001 | Jackson | |
| 6,835,196 | B2 * | 12/2004 | Biedermann et al. | 606/308 |
| 7,204,838 | B2 * | 4/2007 | Jackson | 606/270 |
| 2003/0100896 | A1 | 5/2003 | Biedermann et al. | |
| 2004/0249380 | A1 * | 12/2004 | Glascott | 606/73 |
| 2005/0038432 | A1 | 2/2005 | Shaolian et al. | |
| 2005/0171537 | A1 * | 8/2005 | Mazel et al. | 606/61 |
| 2006/0036244 | A1 | 2/2006 | Spitler et al. | |
| 2006/0149235 | A1 * | 7/2006 | Jackson | 606/61 |

* cited by examiner 40
38
37
33
32
31
42
34

32
33
38
43
44
37
39
35
31
34
42
36

31
35
32

403
405
400
406
401
404

400
406
405
407
402

403
407
405
401
404
402
400

500
501
503
504
502
402
400

LOCKING ASSEMBLY FOR SECURING A ROD MEMBER IN A RECEIVER PART FOR USE IN SPINAL OR TRAUMA SURGERY, BONE ANCHORING DEVICE WITH SUCH A LOCKING ASSEMBLY AND TOOL THEREFOR

CROSS-REFERENCE TO RELATED APPLICATION(S)

The present disclosure claims the benefit of U.S. Provisional Patent Application Ser. No. 60/787,901, filed Mar. 31, 2006, and claims priority from European Patent Application EP06006832.7, filed Mar. 31, 2006, the entire disclosures of which are incorporated herein by reference.

BACKGROUND

The invention relates to a locking assembly for securing a rod member in a receiver part connected to a shank for use in spinal or trauma surgery. The invention further relates to a bone anchoring device using such a locking assembly and to a tool for cooperating with such a locking assembly.

U.S. Pat. No. 6,224,598 B1 discloses a threaded plug closure adapted for use in securing a rod member to a bone screw implant, said closure comprising a plug having a threaded cylindrically-shaped outer surface, said plug being received between a pair of arms of a medical implant during use, a central coaxial bore passing entirely through said plug, said central bore having an internal threaded surface which is shaped to receive a set screw. The plug closure and the set screw can be independently installed and the set screw tightened to cooperatively provide capture and locking of the rod in order to secure the rod against translational and rotational movement relative to the bone screw.

US 2003/0100896 A1 discloses a bone anchoring device with a shank and a receiving part connected to it for connecting to a rod. The receiving part has a recess having a U-shaped cross-section for receiving the rod with two open legs and an internal thread on the open legs. A locking assembly is provided comprising a nut member with an external thread which cooperates with the internal thread of the legs and a set screw. The nut member has on one end slits for engagement with a screw tool. The shank has a spherically shaped head which is pivotably held in the receiving part and a pressure element is provided which exerts pressure on the head when the nut member is tightened. By tightening the set screw the rod is fixed in the receiving part. Hence, the rod and the head can be locked independently from each other. The internal thread and the cooperating external thread of the nut member are designed as a flat thread. The implant has a compact design, since an outer ring or nut to prevent splaying of the legs is not necessary.

The outer diameter of the locking assembly is under various aspects determined by the required tightening torque and the thread form. In turn, the overall dimensions of the upper portion of the bone anchoring device are determined by the size of the locking assembly.

Therefore, there is a need for a locking assembly and a bone anchoring device with a locking assembly which has the same reliability as the known devices but which has smaller dimensions of the upper portion. Furthermore, there is a need for a tool for such a locking assembly.

SUMMARY

The locking assembly according to the invention can be designed with a smaller outer diameter compared to the known locking assemblies. Therefore, the size of the bone anchoring device can be reduced. The bone anchoring device with such a reduced size is particularly suitable for application to the cervical spine or other areas where a limited available space requires compact implants.

Furthermore, the locking assembly is structured so as to allow nesting of two or more locking elements.

With the tool according to the invention a simultaneous but independent fixation of the locking elements of the locking assembly is possible.

Further features and advantages of the invention will become apparent and will be best understood by reference to the following detailed description of embodiments taken in conjunction with the accompanying drawings.

DETAILED DESCRIPTION OF THE INVENTION

Figure 1:
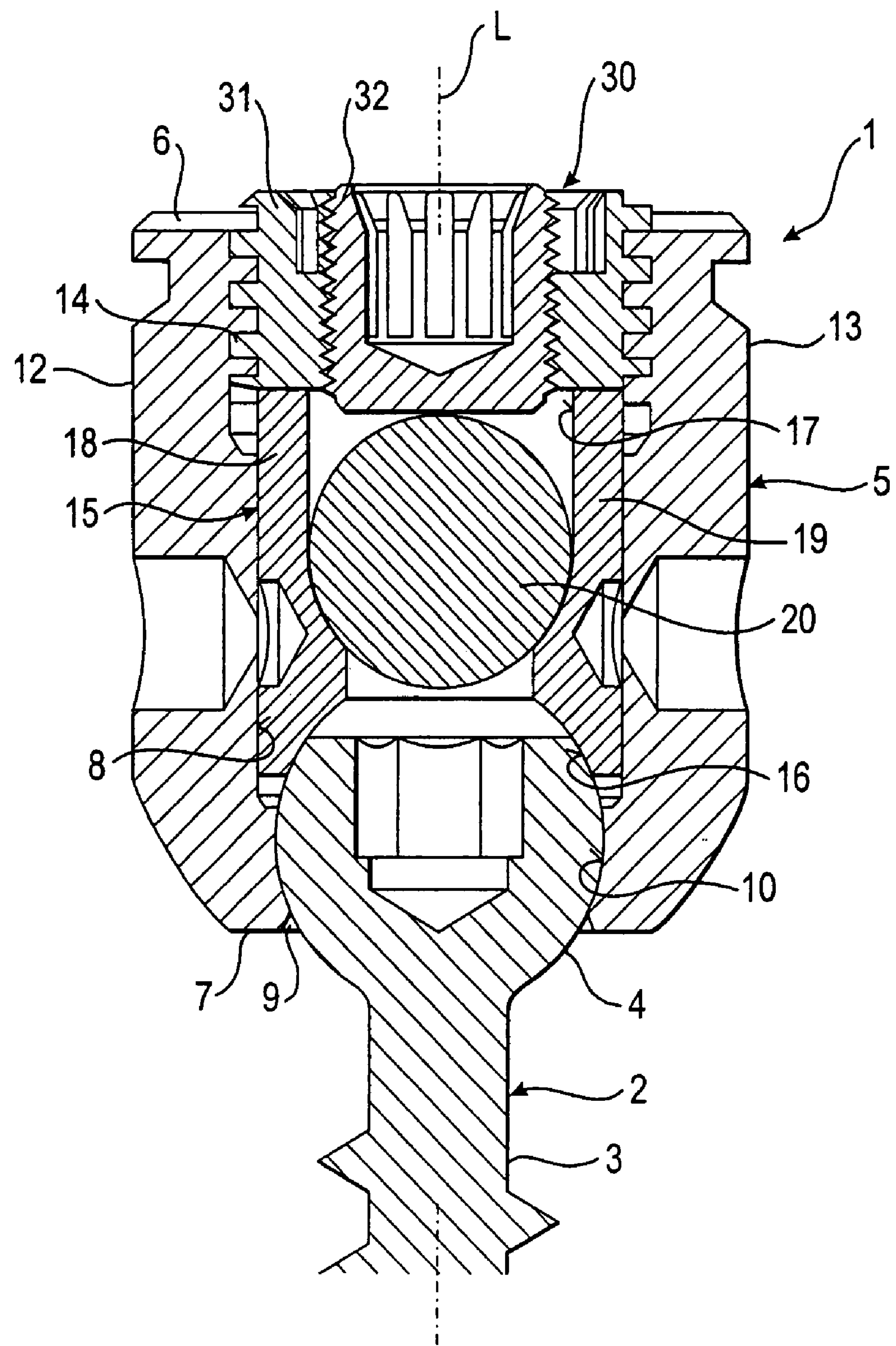
FIG. 1 shows a cross-sectional view of an embodiment of the bone anchoring device with the locking assembly.
Figure 2:
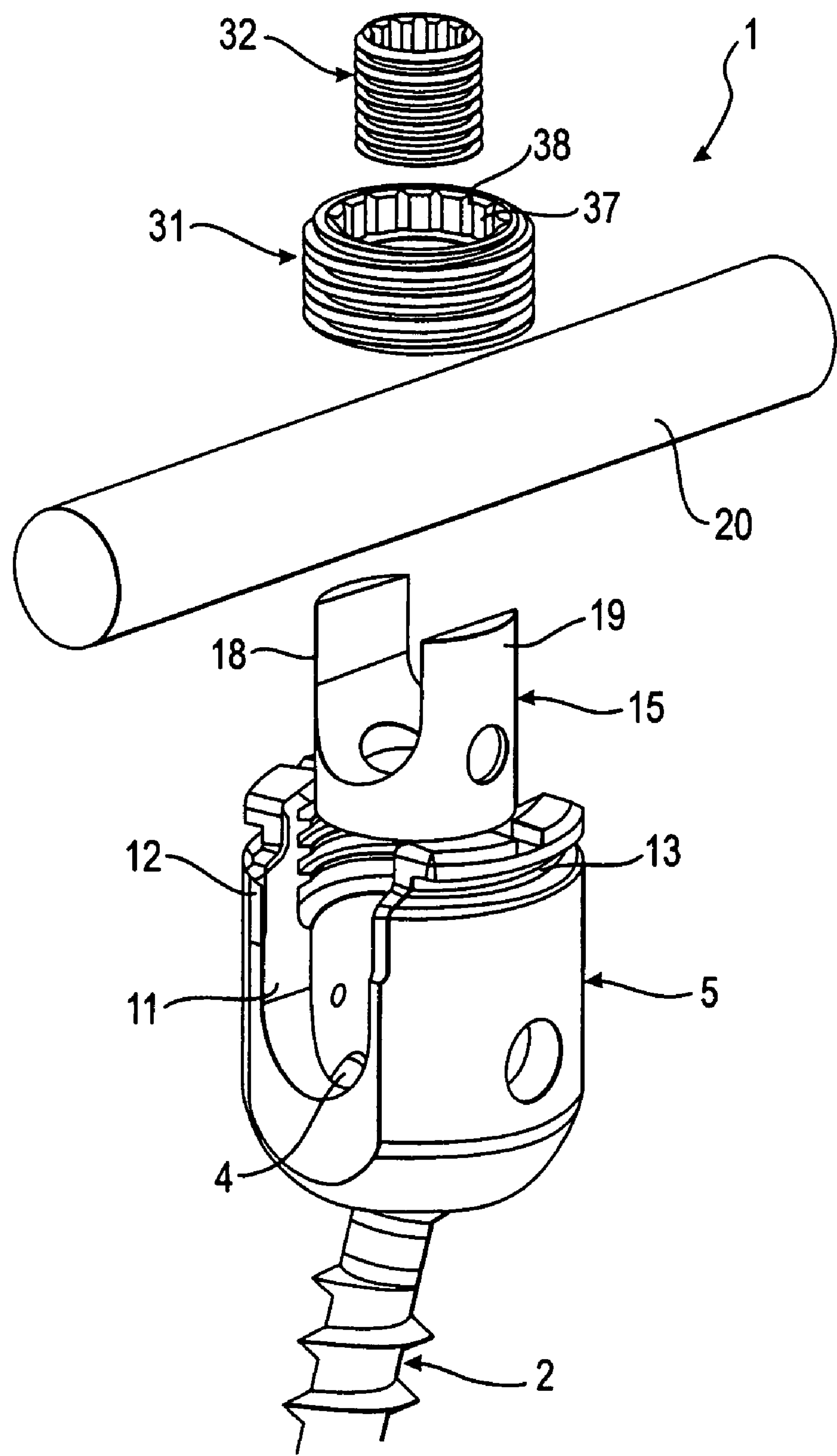
FIG. 2 shows a perspective elevational view of the bone anchoring device of FIG. 1.

FIGS. 1 and 2 show the locking assembly used in a polyaxial bone anchoring device 1. The bone anchoring device comprises a bone screw 2 having a shank 3 with a bone thread and a spherically-shaped head 4. The bone screw 2 is received in a receiving part 5 which has a first end 6 and a second end 7 and is of substantially cylindrical construction. The two ends are perpendicular to a longitudinal axis L. Coaxially with the longitudinal axis L a bore 8 is provided which extends from the first end 6 to a predetermined distance from the second end 7. At the second end 7 an opening 9 is provided, the diameter of which is smaller than the diameter of the bore 8. The coaxial bore 8 tapers towards the opening 9. In the embodiment shown it tapers in form of a spherically shaped section 10. However, the section 10 can have any other shape such as, for example, a conical shape.

The receiving part 5, further, has a U-shaped recess 11 which starts at the first end 6 and extends in the direction of the second end 7 to a predetermined distance from said second end. By means of the U-shaped recess two free legs 12, 13 are formed ending towards the first end 6. Adjacent to the first end 6, the receiving part 5 comprises an internal thread 14 at the inner surface of the legs 12, 13. In the embodiment shown, the internal thread 14 is a flat thread having horizontal upper and lower thread flanks.

Additionally, a pressure element 15 is provided which has a substantially cylindrical construction with an outer diameter sized so as to allow the pressure element 15 to be introduced into the bore 8 of the receiving part and to be moved in the axial direction. On its lower side facing towards the second end 7, the pressure element 15 comprises a spherical recess 16 cooperating with a spherical section of the head 4. On its opposite side the pressure element 15 has a U-shaped recess 17 extending transversely to the longitudinal axis L by means of which two free legs 18,19 are formed. The lateral diameter of this U-shaped recess is selected such that a rod 20 which is to be received in the receiving part 5 can be inserted into the recess 17 and guided laterally therein. The depth of this U-shaped recess 17 is larger than the diameter of the rod 20 so that the legs 18, 19 extend above the surface of the rod 20 when the rod is inserted.

Figure 3:
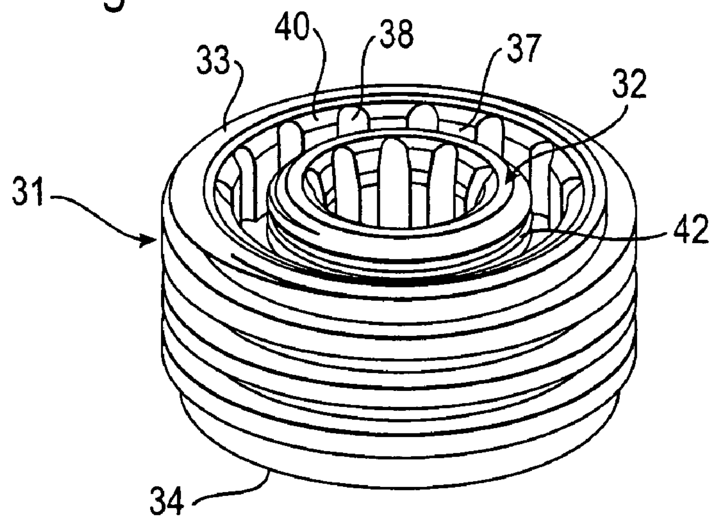
FIG. 3 shows a perspective view from the top of the locking assembly.
Figure 4:
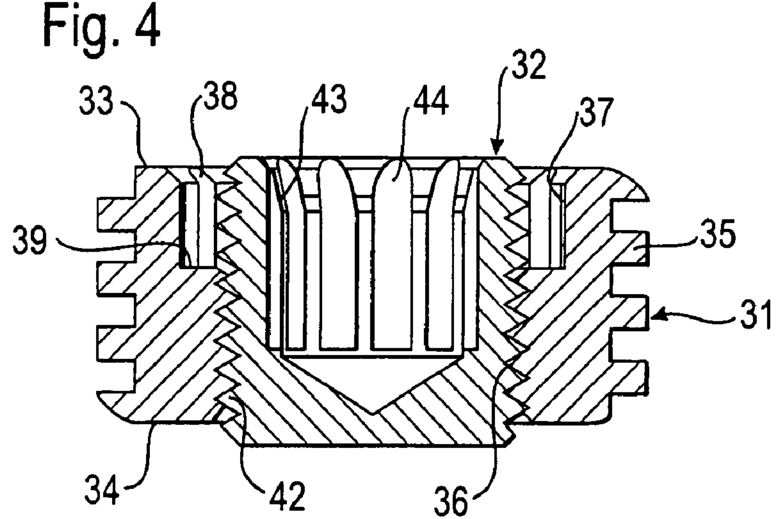
FIG. 4 shows a cross-sectional view of the locking assembly of FIG. 3.
Figure 5:
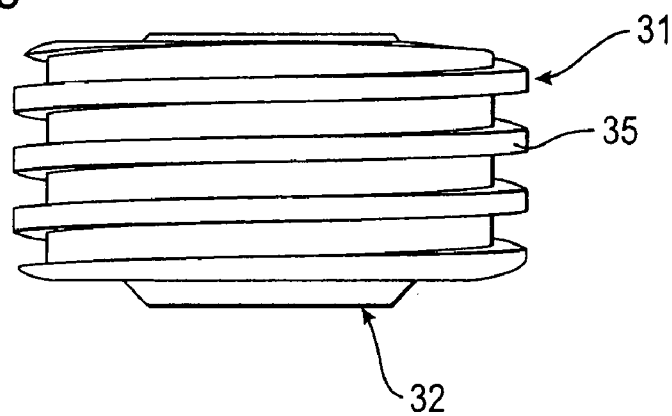
FIG. 5 shows a side view of the locking assembly of FIG. 3.
Figure 6:
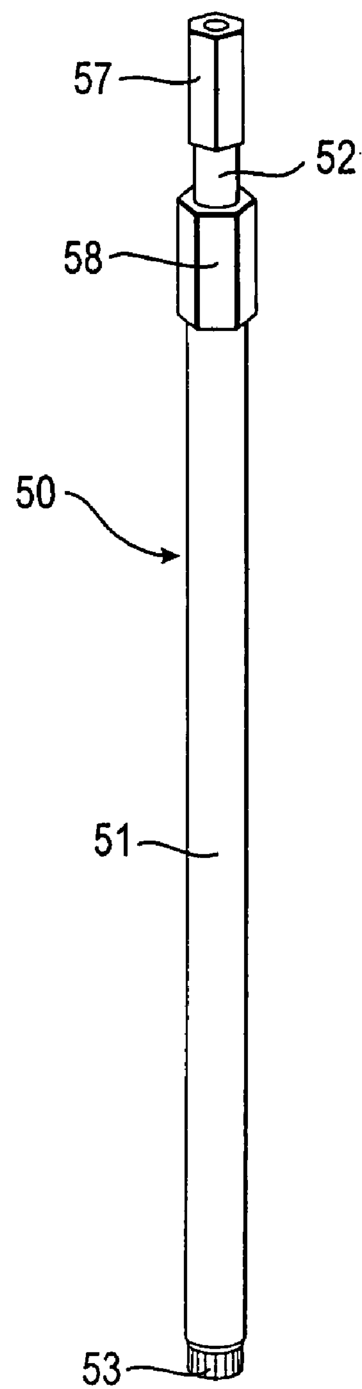
FIG. 6 shows a perspective view of a tool.
Figure 7:
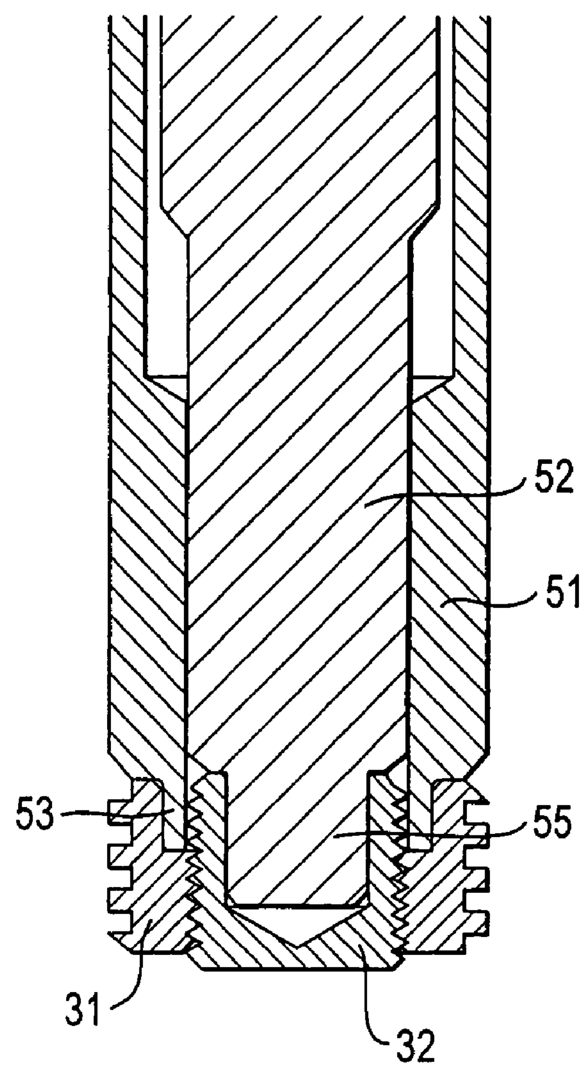
FIG. 7 shows a cross-sectional view of the lower part of the tool cooperating with the locking assembly.
Figure 8:
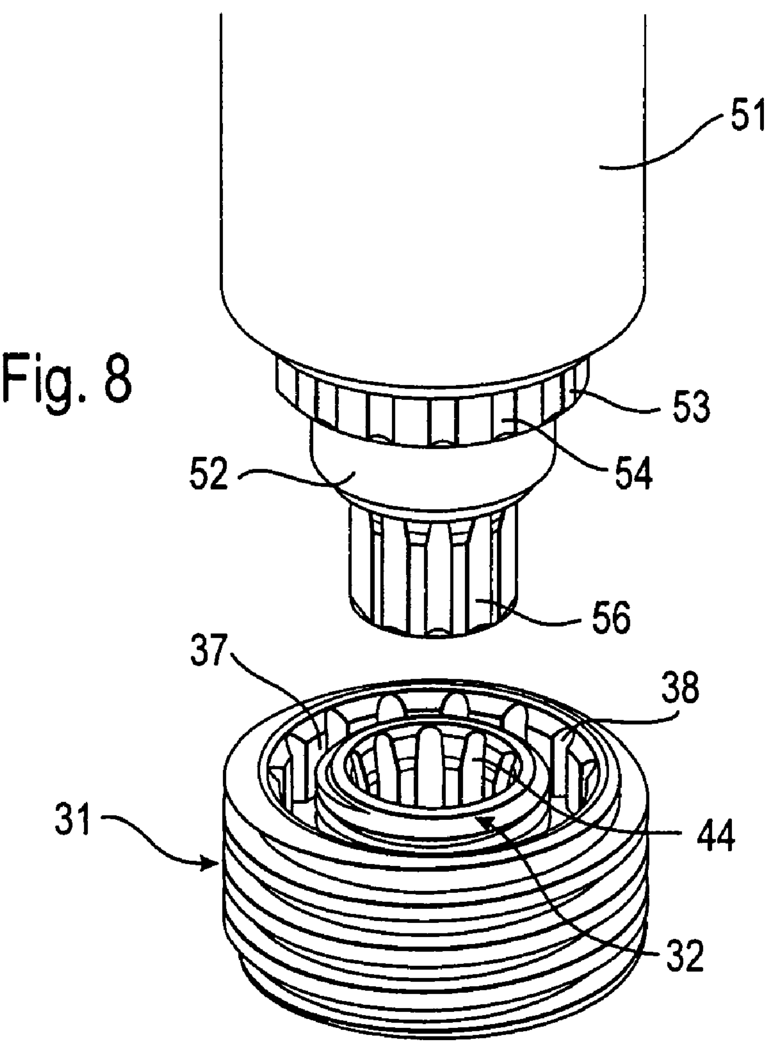
FIG. 8 shows a perspective view of the locking assembly and the lower part of the tool.

The bone anchoring device comprises a locking assembly 30. The locking assembly 30 includes, as shown in particular in FIGS. 2 to 5 a first locking element 31 and a second locking element 32. The first locking element has a first end 33 and a second end 34 and a substantially cylindrical shape between the first and the second end and with an outer surface having an external thread 35 which is, in the embodiment shown, a flat thread which matches with the internal thread 14 of the receiving part 5. Further, the first locking element comprises a coaxial bore 36 extending from the second end 34 in the direction of the first end 33. The coaxial bore 36 comprises an internal thread, which is in the embodiment shown a metric thread. The first locking element 31 further comprises a coaxial recess 37 starting from the first end 33 and extending to a predetermined distance from the second end 34. The mean diameter of the recess 37 is larger than the diameter of the coaxial bore 36. As can be seen in particular in FIG. 3, by means of the recess 37 a substantially ring-shaped wall is formed. A plurality of longitudinal grooves 38 are formed extending from the first end 33 along the wall to the bottom 39 of the recess 37. The grooves 38 shown in this embodiment have an approximately semi-circular cross section. They are equidistantly distributed in a circumferential direction of the recess 37. Preferably, at least two grooves are formed. The wall of the recess 37 can have a slanted surface 40 adjacent to the first end 33 in order to facilitate the introduction of a tool. The depth of the recess 37 is selected such that the length of the bore 36 is still sufficient to cooperate with the second locking element 32 for a good fixation. On the other hand the depth of the recess 37 is such that an area sufficient for engagement with a tool is provided.

The second locking element 32 is shaped as a set screw with an external thread 42 cooperating with the internal thread of the coaxial bore 36. The axial length of the second locking element 32 is such that when the second locking element 32 is completely screwed into the first locking element 31 it projects slightly from the second end 34 of the first locking element. As can be seen in particular in FIG. 4, the second locking element 32 comprises a coaxial recess 43 with grooves 44 extending in longitudinal direction, similar to the recess 37 and the grooves 38 of the first locking element. The recess 43 and the grooves 44 serve for a form-fit cooperation with a tool to be described hereinafter.

A tool for cooperating with the locking assembly is shown in FIGS. 6 to 9. The tool 50 comprises a tube 51 and a bar 52 which is slidable in the tube 51. The tube 51 has an end section 53 for cooperation with the locking assembly and a second end with a grip portion 58 which has, for example, a hexagonal outer shape. As can be seen in particular in FIGS. 7 to 9, the end section 53 has a reduced outer diameter, corresponding to the inner diameter of the recess 37 of the first locking element. The end section 53 comprises a plurality of projections 54 the number of which is less than or equal to the number of the grooves 38 of the first locking element. The projections 54 are structured and designed to engage with the grooves 38 of the first locking element to provide a form-fit connection between the end section 53 of the tool and the recess 37 of the first locking element. The axial length of the end section 53 is preferably equal to or larger than the depth of the recess 37.

The bar 52 comprises an end section 55 which is structured and designed to cooperate with the recess 43 of the second locking element 32. For this purpose, the end section 55 has a plurality of projections 56 the number of which is equal to or less than the number of grooves 44 of the second locking element and which are structured and designed to engage with the grooves 44. On its opposite end, the bar 52 has a grip portion 57 which allows to grip the bar 52 and to rotate it independently from the tube 51. The length of the bar 52 is selected such that when the end section 53 of the tube is engaged with the first locking element, the second locking element 32 can be independently engaged by the end section 55 of the bar and screwed into the first locking element.

In operation, first, at least two usually preassembled bone anchoring devices comprising the bone screw 2, the receiving part 5 and the pressure element 15 are screwed into the bone. Thereafter, the rod 20 is inserted into the U-shaped recess 11 of the receiving part 5. Then, the locking assembly 30, comprising the first locking element 31 and the second locking element 32 which are preferably preassembled, is screwed-in between the legs 12, 13 of the receiving part 5. The first locking element is tightened by applying the tool 50 such that the end section 53 of the tube engages with the recess 37 and the grooves 38 of the first locking element to form a form-fit connection. In this way, pressure is exerted by the lower side of the first locking element onto the free legs 18, 19 of the pressure element which presses onto the head 4 of the bone screw 2 to lock the head in its rotational position relative to the receiving part 5.

Then, the second locking element 32 is tightened by application of the tool in that the end section 56 of the bar engages the recess 43 of the second locking element and torque is applied. In this way, the position of the rod 20 relative to the receiving part is fixed.

A fine tuning of the position of the receiving part 5 relative to the bone screw 2 and of the rod 20 relative to the receiving part can be performed by loosening either the first locking element 31 or the second locking element 32.

Figure 9:
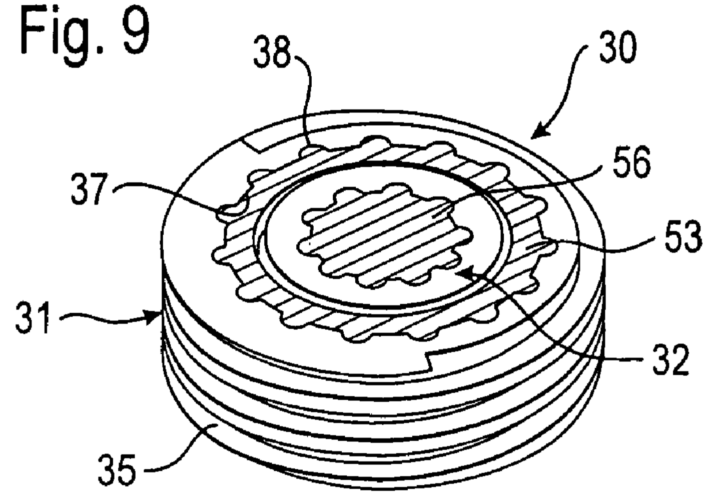
FIG. 9 shows a perspective view of the locking assembly with cooperating portions of the tool shown in section wherein the other parts of the tool are omitted.

FIG. 9 shows a perspective view of the locking assembly 30 with the end sections 53 and 56 of tool engaging the locking elements with the tool shown in section. For the purpose of illustration only, the remainder of the tool is not shown. As can be seen in FIG. 9, the end sections of the tool and the recesses of the first and second locking elements form a form-fit connection for the application of torque to screw-in the locking elements. The external thread 35 of the first locking element is of continuous form, without recesses or interruptions. Therefore, the dimension of the locking element can be reduced. This guarantees safe locking of the first locking element. The area required for engagement of the tool with the first locking element is located within the recess 37. This allows to design the first locking element 31 with a reduced diameter. If the number of grooves 38 is increased, the depth of the grooves can be reduced. Hence, the size of the first locking element can be reduced corresponding to the increase of the number of grooves.

The size of the outer dimension of the first locking element 31 determines the size of the receiving part and the other elements of the bone anchoring device. Further, since the external thread of the first locking element remains intact over its whole length, the height of the locking element can be reduced.

Figure 10:
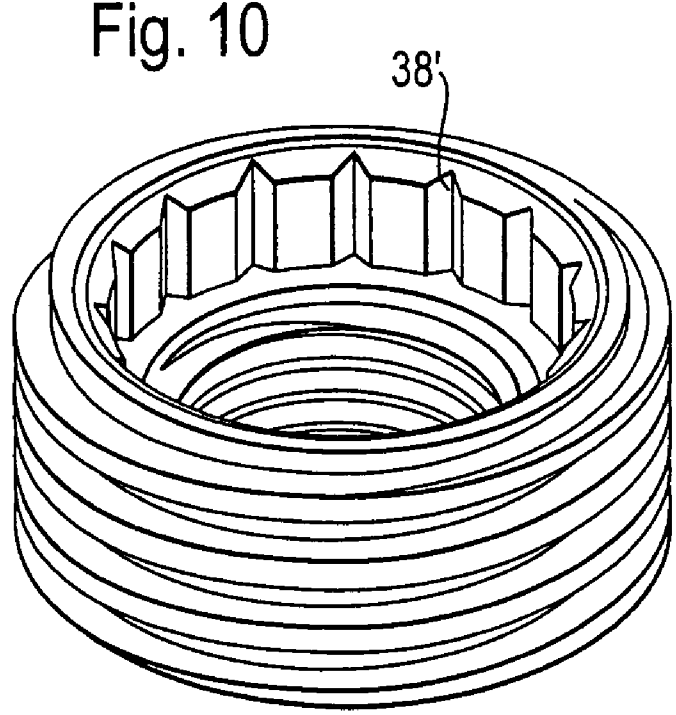
FIG. 10 shows a perspective view of a modification of the first locking element of the locking assembly.
Figure 11:
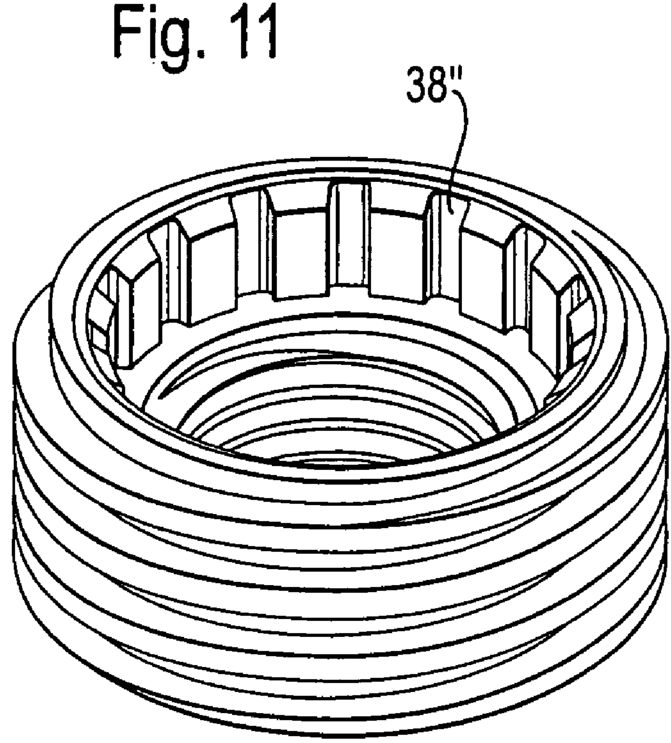
FIG. 11 shows a perspective view of a further modification of the first locking element of the locking assembly.

FIG. 10 shows the first locking element 31 with a modified shape of the grooves. The grooves 38' have a triangular cross section. FIG. 11 shows the first locking element 31 with a further modification of the shape of the grooves. The grooves 38" have a square cross section. However, the cross section of the grooves may have another shape as well.

Figure 12:
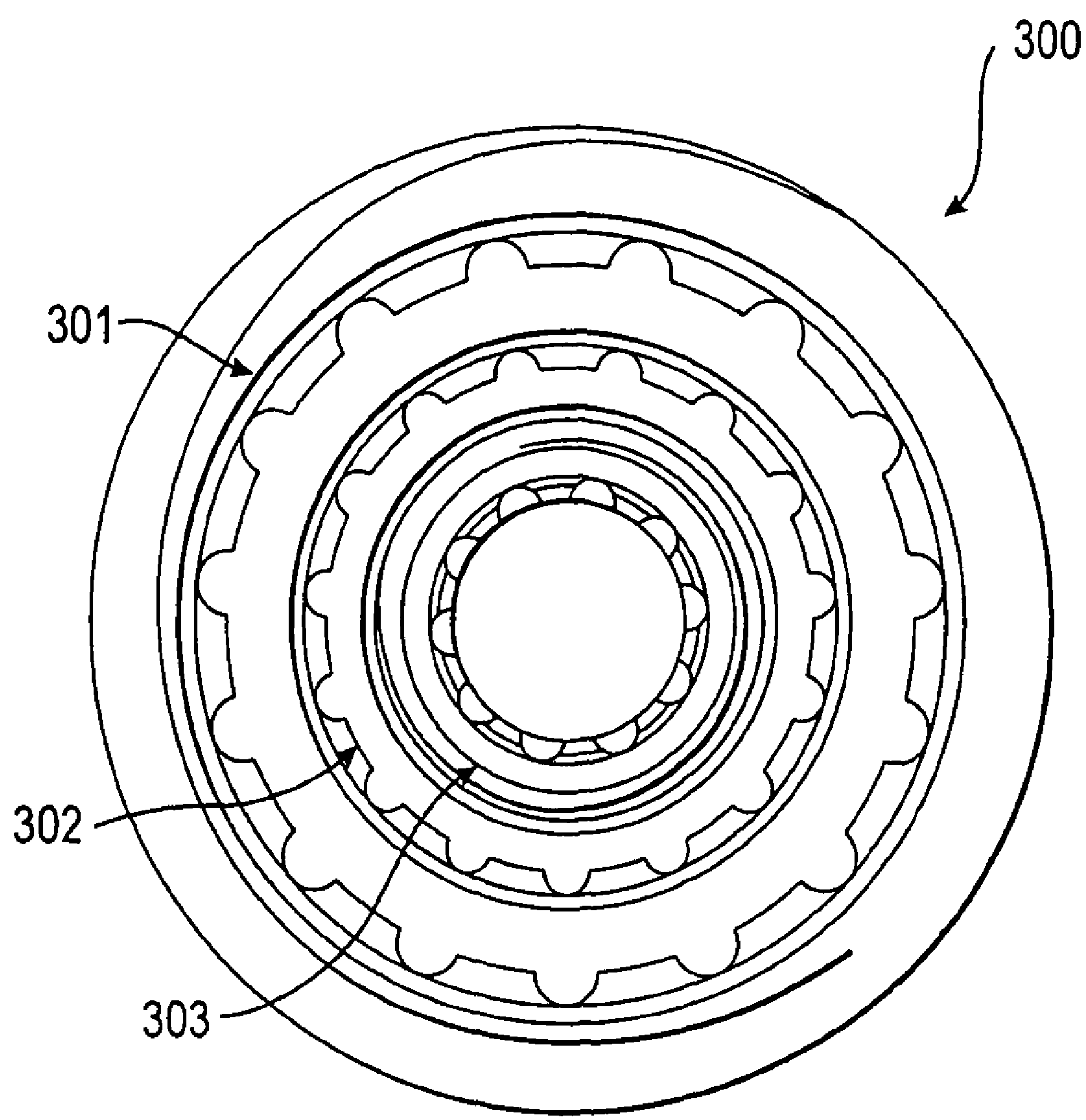
FIG. 12 shows a second embodiment of the locking assembly in a top view.
Figure 13:
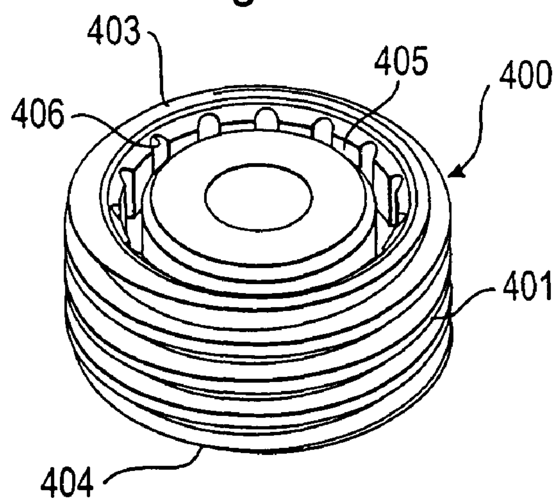
FIG. 13 shows a further embodiment of the locking assembly in a perspective view.
Figure 14:
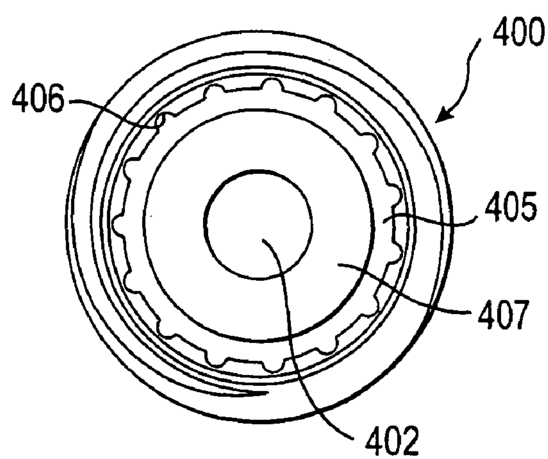
FIG. 14 shows the locking assembly of FIG. 13 in a top view.
Figure 15:
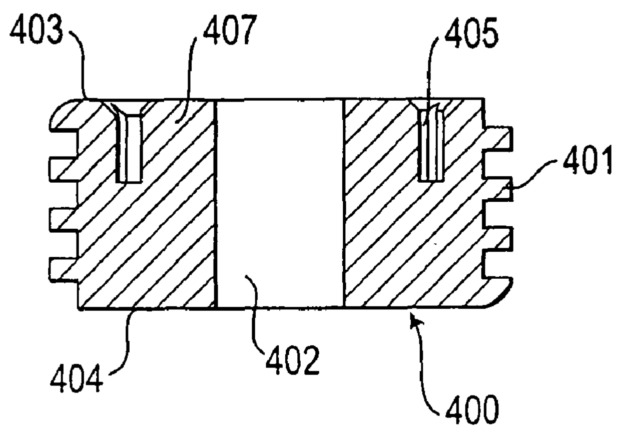
FIG. 15 shows the locking assembly of FIG. 13 in a sectional view along line A-A of FIG. 14.

FIG. 12 shows a second embodiment of the locking assembly. The locking assembly 300 comprises three locking elements. The first locking element 301 is shaped like the locking element 31 of the first embodiment. The second locking element 302 differs from the second locking element 30 of the first embodiment in that is has coaxial threaded bore, like the first locking element, to receive the third locking element 303. It is also possible to design the locking assembly with more than three nested locking elements such that each of the locking elements has a threaded coaxial bore to receive a further locking element. In this manner, for certain applications, an improved fixation can be achieved, for example, if used in complex minimally invasive surgery procedures.

The locking assembly according to a further embodiment includes one single locking element 400 which has an external thread 401 and a coaxial bore 402 extending through the entire locking element from the first end 403 to the second end 404. A coaxial ring-shaped recess 405 extends from the first end 403 in the direction of the second end. The wall of the recess comprises a plurality of longitudinal grooves 406 for engagement with a tool. By means of the recess 405 and the coaxial bore 402, a coaxial hollow cylindrical section 407 is formed in the locking element.

Figure 16:
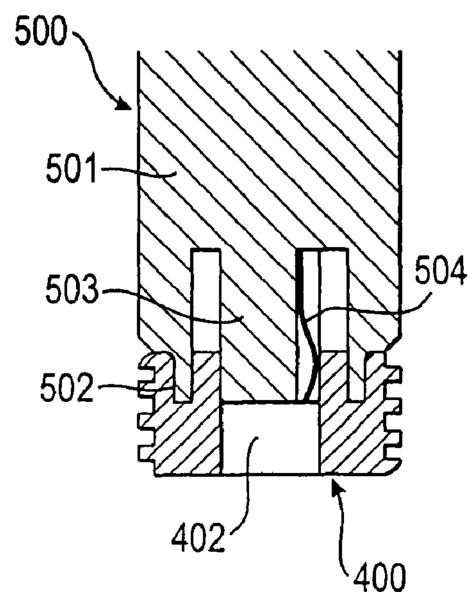
FIG. 16 shows a tool cooperating with the locking assembly of FIG. 13 in a sectional view.

A tool for engagement with the locking element is adapted to be engageable with the ring-shaped recess 405. FIG. 16 shows an exemplary tool 500 cooperating with the locking element 400. The end section 501 comprises a ring-shaped projection 502 adapted to engage the recess 405 in a form-fitting manner. The end section also 501 comprises a central projection 503 with a retaining spring 504 engaging the coaxial bore 402 for facilitating alignment and handling of the locking element.

The locking element can be used in such applications where it is necessary to introduce an instrument or a wire through the bore 402, for example in the case of minimally invasive surgery.

Further modifications are possible. The external and the internal thread can have any thread shape, such as, for example, a metric thread. Using a flat thread, a saw-tooth thread or a negative angle thread for the external thread of the first locking element and the cooperating internal thread of the receiving part, however, has the advantage that it prevents splaying of the legs of the receiving part. Therefore, an outer ring or a nut to prevent splaying is not needed. By using the locking assembly of the invention together with a flat thread as the external thread, the implant can be further downsized.

The number of the grooves and the shape of the grooves can vary.

It is conceivable to design the first locking element with a recess having a quadrangular or hexagonal or otherwise polygonal cross section with or without grooves. In this case, the end section of the tool has a matching shape. This also provides for a form-fit connection between the tool and the first locking element with the external thread of the first locking element remaining intact.

The second locking element 32 or the third locking element 303 in the case of the locking assembly 300 of the second embodiment or, in general, the inmost locking element in the case of a locking assembly having multiple locking elements may not need to have a recess with grooves as shown in the embodiment. It is sufficient, that the inmost locking element has a recess for engagement with screwing-in tool, such as a hexagon recess. The corresponding end section of the tool is then adapted to this shape.

The disclosure is not limited to the polyaxial bone anchoring device as shown in the first embodiment. It can be used in the case of a monoaxial bone anchoring device in which the receiving part is fixedly connected to the shank of the bone screw as well. Furthermore, the polyaxial bone anchoring device can have a different construction. It is possible to have a design of the receiving part which allows that the screw is inserted from the bottom instead from the top of the receiving part.

The locking assembly can also be used in such kind of bone anchoring devices in which the receiving part is designed and structured so that the rod is fixed laterally apart from the central axis of the bone screw.

What is claimed is:

1. A locking assembly for securing a rod in a receiving part of a bone anchoring device for use in spinal or trauma surgery, said locking assembly comprising:

a first locking element having a first end and a second end and a longitudinal axis and an outer surface provided with an external thread, a coaxial bore passing entirely through said first locking element and an internal thread provided at said bore, a second locking element having a first end and a second end, a longitudinal axis and an outer surface with an external thread cooperating with the internal thread of said first locking element, wherein the first end has an engagement structure configured for engagement with a tool to permit rotation of the second locking element, wherein said first locking element has a recess extending from the first end in the direction of the second end and terminating in an annular bottom surface extending transverse to the longitudinal axis, said recess defining a circumferentially closed wall portion, wherein the interior of the wall portion has a longitudinally extending structure for engagement with a tool; and wherein when the first end of the second locking element is aligned with the first end of the first locking element, the second locking element can be independently engaged and screwed into and out of the first locking element and the first locking element can be independently engaged and screwed into and out of the receiving part.

2. The locking assembly of claim 1, wherein said structure comprises a plurality of longitudinally extending recesses provided in the wall portion.

3. The locking assembly of claim 1, wherein said structure comprises a plurality of longitudinally extending grooves provided in the wall portion.

4. The locking assembly of claim 1, wherein the external thread of the first locking element is intact over its whole axial length.

5. The locking assembly of claim 1, wherein the external thread of the first locking element is designed as a flat thread.

6. The locking assembly of claim 1, wherein said second locking element is designed as a set screw.

7. The locking assembly of claim 1, wherein said first locking element is shaped to be entirely received in the receiving part of the bone anchoring device.

8. The locking assembly of claim 1, wherein said second locking element comprises a coaxial bore provided with an internal thread to receive a third locking element with an external thread cooperating with the internal thread.

9. The locking assembly of claim 1, wherein said second locking element has a first end and a second end and a recess extending from the first end in the direction of the second end, said recess having an interior wall portion with a plurality of longitudinally extending grooves.

10. The locking assembly of claim 1, further comprising a tool, wherein the tool comprises a first tool portion with a longitudinal axis of rotation and with a structure for engagement with the longitudinal structure of the recess of the first locking element.

11. The locking assembly of claim 10, wherein the tool comprises a second tool portion for engagement with the second locking element, the first and the second tool portions being rotatable independently from each other.

12. The locking assembly of claim 11, wherein the first tool portion is the end section of a tube and the second tool portion is the end section of a bar which is slidable in the tube.

13. A bone anchoring device comprising:

a shank to be anchored in a bone;

a receiving part coupled to the shank and configured to receive a rod, the receiving part comprising a recess having a substantially U-shaped cross section for receiving the rod with two open legs on one end and an internal thread on the open legs; and a locking assembly comprising:

a first locking element having a first end and a second end and a longitudinal axis and an outer surface provided with an external thread, a coaxial bore passing entirely through said first locking element and an internal thread provided at said bore, a second locking element having a first end and a second end, a longitudinal axis and an outer surface with an external thread cooperating with the internal thread of said first locking element, wherein the first end has an engagement structure configured for engagement with a tool to permit rotation of the second locking element, wherein said first locking element has a recess extending from the first end in the direction of the second end and terminating in an annular bottom surface extending transverse to the longitudinal axis, said recess defining a circumferentially closed wall portion, wherein the interior of the wall portion has a longitudinally extending structure for engagement with a tool;

wherein when the first end of the second locking element is aligned with the first end of the first locking element, the second locking element can be independently engaged and screwed into and out of the first locking element and the first locking element can be independently engaged and screwed into and out of the receiving part; and wherein the external thread of the first locking element cooperates with the internal thread provided on said legs.

14. The bone anchoring device of claim 13, wherein said shank is pivotably or rotatably connected to said receiving part and wherein said first locking element acts directly or indirectly onto said shank to lock the position of said shank relative to said receiving part.

15. The bone anchoring device of claim 14, wherein said shank comprises a spherically-shaped end portion and wherein the first locking element acts on said end portion via a pressure element.

16. The bone anchoring device of claim 13, wherein said second locking element acts on said rod to fix the position of said rod relative to the receiving part.

17. A locking assembly for securing a rod in a receiving part of a bone anchoring device for use in spinal or trauma surgery, said locking assembly comprising:

a first locking element having a first end and a second end and a longitudinal axis of rotation and a substantially cylindrical outer surface provided with an external thread, a coaxial bore passing entirely through said first locking element and an internal thread provided at said bore, a second locking element having a longitudinal axis of rotation and a substantially cylindrical outer surface with an external thread cooperating with the internal thread of said first locking element, wherein said first locking element has a recess extending from the first end in the direction of the second end and terminating in an annular bottom surface extending transverse to the longitudinal axis, said recess defining a circumferentially closed wall portion, wherein the interior of the wall portion has a longitudinally extending structure for engagement with a tool; and wherein an axial length of the second locking element is larger than an axial length of the first locking element.

18. The locking assembly of claim 17, wherein said structure comprises a plurality of longitudinally extending recesses provided in the wall portion.

19. The locking assembly of claim 17, wherein said structure comprises a plurality of longitudinally extending grooves provided in the wall portion.

20. The locking assembly of claim 17, wherein the external thread of the first locking element is intact over its whole axial length.

21. The locking assembly of claim 17, wherein the external thread of the first locking element is designed as a flat thread.

22. The locking assembly of claim 17, wherein said second locking element is designed as a set screw.

23. The locking assembly of claim 17, wherein said first locking element is shaped to be entirely received in the receiving part of the bone anchoring device.

24. The locking assembly of claim 17, wherein said second locking element comprises a coaxial bore provided with an internal thread to receive a third locking element with an external thread cooperating with the internal thread.

25. The locking assembly of claim 17, wherein said second locking element has a first end and a second end and a recess extending from the first end in the direction of the second end, said recess having an interior wall portion with a plurality of longitudinally extending grooves.

26. The locking assembly of claim 17, further comprising a tool, wherein the tool comprises a first tool portion with a longitudinal axis of rotation and with a structure for engagement with the longitudinal structure of the recess of the first locking element.

27. The locking assembly of claim 26, wherein the tool comprises a second tool portion for engagement with the second locking element, the first and the second tool portions being rotatable independently from each other.

28. The locking assembly of claim 27, wherein the first tool portion is the end section of a tube and the second tool portion is the end section of a bar which is slidable in the tube.

29. A bone anchoring device comprising:

a shank to be anchored in a bone;

a receiving part coupled to the shank and configured to receive a rod, the receiving part comprising a recess having a substantially U-shaped cross section for receiving the rod with two open legs on one end and an internal thread on the open legs; and a locking assembly comprising:

a first locking element having a first end and a second end and a longitudinal axis of rotation and a substantially cylindrical outer surface provided with an external thread, a coaxial bore passing entirely through said first locking element and an internal thread provided at said bore, a second locking element having a longitudinal axis of rotation and a substantially cylindrical outer surface with an external thread cooperating with the internal thread of said first locking element, wherein said first locking element has a recess extending from the first end in the direction of the second end and terminating in an annular bottom surface extending transverse to the longitudinal axis, said recess defining a circumferentially closed wall portion, wherein the interior of the wall portion has a longitudinally extending structure for engagement with a tool;

wherein an axial length of the second locking element is larger than an axial length of the first locking element; and wherein the external thread of the first locking element cooperates with the internal thread provided on said legs.

30. The bone anchoring device of claim 29, wherein said shank is pivotably or rotatably connected to said receiving part and wherein said first locking element acts directly or indirectly onto said shank to lock the position of said shank relative to said receiving part.

31. The bone anchoring device of claim 30, wherein said shank comprises a spherically-shaped end portion and wherein the first locking element acts on said end portion via a pressure element.

32. The bone anchoring device of claim 29, wherein said second locking element acts on said rod to fix the position of said rod relative to the receiving part.

* * * * *